(12) United States Patent
Brunsvik et al.

(10) Patent No.: US 8,492,707 B2
(45) Date of Patent: Jul. 23, 2013

(54) METHOD OF DETECTING PNEUMOCANDIN COMPOUNDS

(75) Inventors: Anders Brunsvik, Trondheim (NO); Martin Mansson, Oslo (NO)

(73) Assignee: Xellia Pharmaceuticals APS (DK)

( * ) Notice: Subject to any disclaimer, the term of this patent is extended or adjusted under 35 U.S.C. 154(b) by 0 days.

(21) Appl. No.: 13/389,598

(22) PCT Filed: Aug. 11, 2010

(86) PCT No.: PCT/NO2010/000302
§ 371 (c)(1),
(2), (4) Date: Feb. 9, 2012

(87) PCT Pub. No.: WO2011/019286
PCT Pub. Date: Feb. 17, 2011

(65) Prior Publication Data
US 2012/0138786 A1 Jun. 7, 2012

Related U.S. Application Data

(60) Provisional application No. 61/233,846, filed on Aug. 14, 2009.

(51) Int. Cl.
*B01D 59/44* (2006.01)
*H01J 49/00* (2006.01)

(52) U.S. Cl.
USPC ........... 250/281; 250/283; 250/287; 250/288; 250/290; 250/291; 250/292; 250/293; 530/315; 530/320; 530/321

(58) Field of Classification Search
USPC .. 250/281–283, 287, 288, 290–293; 530/315, 530/320, 321
See application file for complete search history.

(56) References Cited

U.S. PATENT DOCUMENTS

| 5,021,341 A | 6/1991 | Giacobbe et al. |
| 5,194,377 A | 3/1993 | Schwartz |
| 2012/0142893 A1* | 6/2012 | Brunsvik ...................... 530/321 |

OTHER PUBLICATIONS

Adefarati et al.; "Pneumocandins from Zalerion Arboricola, V. Glutamic Acid and Leucine-Derived Amino Acids in PneumocandinA0 (L-671,329) and Distinct Origins of the Substituted Proline Resides in Pneumocandins A0 and B0"; The Journal of Antibiotics; 45(12); pp. 1953-1957; (1992).

Egle, et al.; "An Advanced Double Column-Switching Technique (LC-LC) for Liquid Chromatography/Electrospray Ionisation Tandem Mass Spectrometry for Fully Automated Analysis of Caspofungin"; Rapid Commun. Mass Spectrom.; 18; pp. 2871-2877; (2004).

Hensens et al.; "Pneumocandins From Zalerion Arboricola, III. Structure Elucidation"; The Journal of Antibiotics; 45 (12); pp. 1875-1885; (1992).

International Search Report and Written Opinion; International Filing Date Aug. 11, 2010; Date of Mailing Oct. 15, 2010; 15 pages.

Masurekar et al.; "Pneumocandins From Zalerion Arboricola, II. Modification of Product Spectrum by Mutation and Medium Manipulation"; The Journal of Antibiotics; 45(12); pp. 1867-1874; (1992).

(Continued)

*Primary Examiner* — Nikita Wells
*Assistant Examiner* — Meenakshi Sahu
(74) *Attorney, Agent, or Firm* — Cantor Colburn LLP

(57) ABSTRACT

The present invention concerns a method of detecting the antifungal cyclic hexapeptides Pneumocandin $B_0$ and/or Pneumocandin $C_0$ specific fragment is/are detected using MS in negative mode.

13 Claims, 16 Drawing Sheets

OTHER PUBLICATIONS

Qin et al.; "Collision-Induced Dissociation of Protonated MK-0991: Novel Ring Opening of a Cyclic Hexapeptide in the Gas Phase"; Journal of Mass Spectrometry; 34; pp. 733-740; (1999).

Schmatz et al.; "Pneumocandins From Zalerion Arboricola, IV. Biological Evaluation of Natural and Semisynthetic Pneumocandins for Activity Against *Pneumocystis carinii* and *Candida* Species"; The Journal of Antibiotics; 45(12); pp. 1886-1891; (1992).

Schwartz et al.; "Pneumocandins From Zalerion Arboricola"; The Journal of Antibiotics; 45(12); pp. 1853-1866; (1992).

Osawa AE et al, "Purification of pneumocandins by preparative silica gel high performance liquid chromatography", Journal of Chromotography, vol. 831, No. 2, (Jan. 29, 1999), pp. 217-225.

Van Den Broek et al, "Quantitative bioanalysis of peptides by liquid chromatography coupled to (tandem) mass spectrometry", J. Chromatography, vol. 872, No. 1-2, (! Sep. 2008) pp. 1-22.

Rochat et al, "Liquid chromatography-mass spectrometry method for quantification of caspfungin in clinical plasma samples", J Mass Spectrom vol. 42, No. 4 (Apr. 4, 2007) pp. 440-449.

\* cited by examiner

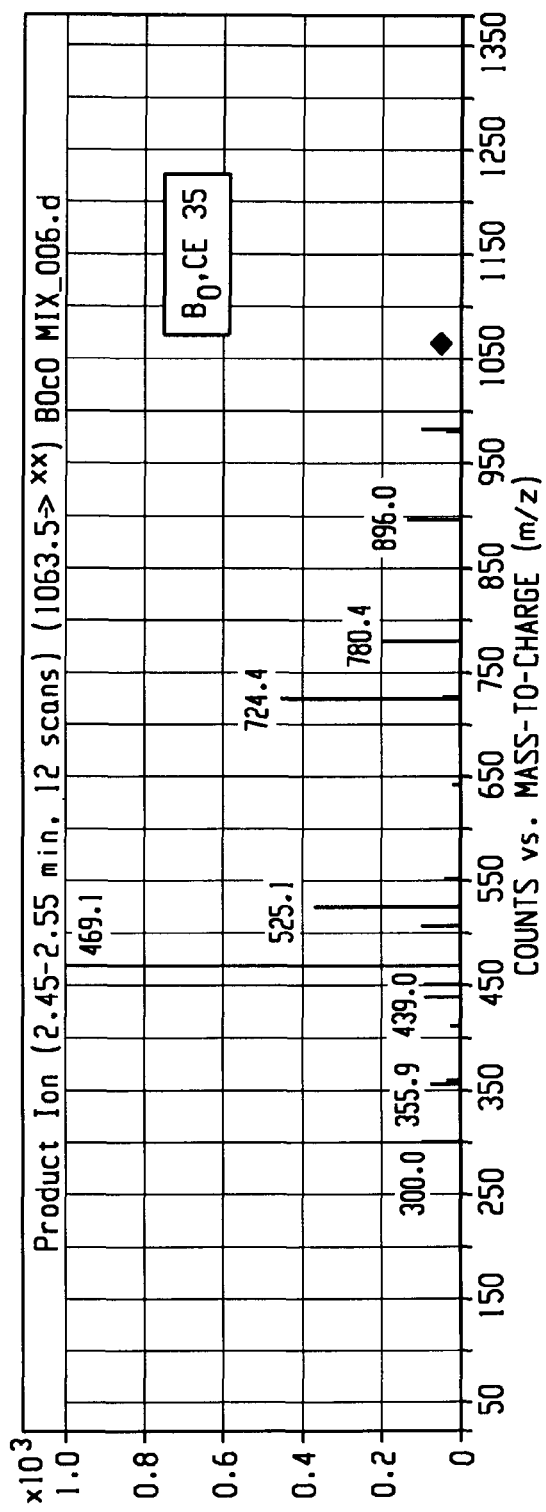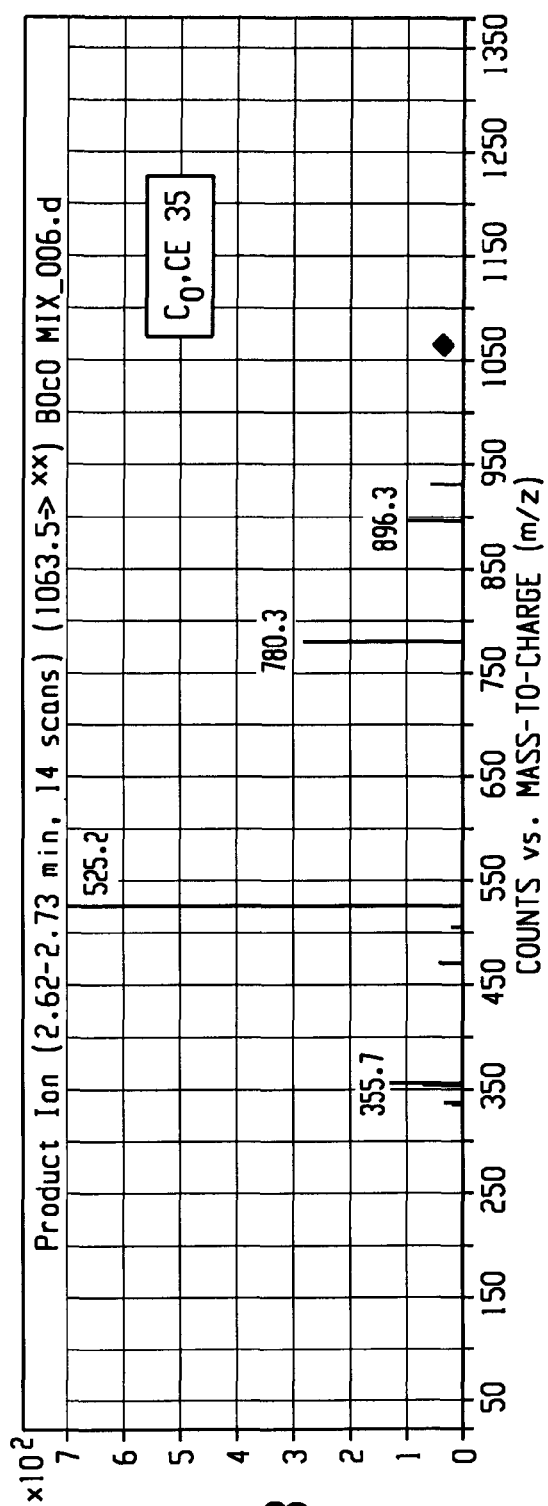
Fig. 5A
Fig. 5B

METHOD OF DETECTING PNEUMOCANDIN COMPOUNDS

FIELD OF THE INVENTION

The present invention concerns methods of detecting Pneumocandin compounds.

BACKGROUND

Pneumocandins are antifungal cyclic hexapeptides with a lipid side chain (see Schwarts et al, 1992, Journal of antibiotics, Vol 45, No 12, pages 1853-1866, Masurekar et al, 1992, Journal of Antibiotics, Vol 45, No. 12, pages 1867-1874, Hensens et al, 1992, Journal of Antibiotics, Vol 45, No 12, pages 1875-1885, Schmatz et al, 1992, Journal of Antibiotics, Vol 45, No 12, pages 1886-1891 and Adefarati et al, 1992, Journal of Antibiotics, Vol 45, No 12, pages 1953-1957 and U.S. Pat. No. 5,021,341)

The antifungal activity of Pneumocandins is connected to inhibition of the biosynthesis of 1,3β-glucans. 1,3β-glucan synthase, a multisubunit enzyme, is responsible for fungal cell wall construction, division septum deposition, and ascospore wall assembly. The catalytic subunit of this enzyme complex, an integral membrane protein, has been identified both in model yeasts *Saccharomyces cerevisiae* and *Schizosaccharomyces pombe*, and in pathogenic fungi such as *Candida, Aspergillus, Cryptococcus* and *Pneumocystis* species". (Curr Drug Targets Infect Disord. 2001 August; 1(2): 159-69 by Liu and Balasubramanian).

The Pneumocandins and Pneumocandin derivatives are useful as active pharmaceutical ingredients (APIs) and/or intermediates for producing APIs. Drugs comprising the APIs are intended for use in therapeutic or prophylactic treatment of diseases or conditions involving fungal infections.

For example, the API Caspofungin is a semi synthetic derivative of Pneumocandin $B_0$. Caspofungin, marketed as Cancidas®, is indicated in adults and pediatric patients (3 months and older) for:

- Empirical therapy for presumed fungal infections in febrile, neutropenic patients.
- Treatment of Candidemia and the following Candida infections: intra-abdominal abscesses, peritonitis and pleural space infections.
- Treatment of Esophageal Candidiasis.
- Treatment of Invasive Aspergillosis in patients who are refractory to or intolerant of other therapies Thus, high purity of the API is required for safety and efficacy of the drugs.

Pneumocandin $B_0$ can be used as a starting material for producing Caspofungin. During such production, Pneumocandin $C_0$ will be regarded as an impurity. Thus it is desirable to monitor and control both the content of Pneumocandin $B_0$ as well as the content of Pneumocandin $C_0$.

Pneumocandin $B_0$ is often produced by fermentation of the fungus *Glarea lozoyensis* (earlier classified as *Zalerion arboricola*), but many isomers and derivatives with similar physiochemical properties, are coproduced in the fermentation processes.

Pneumocandin $B_0$ and Pneumocandin $C_0$ are isomers which differ by the position of one hydroxyl group at a proline residue only:

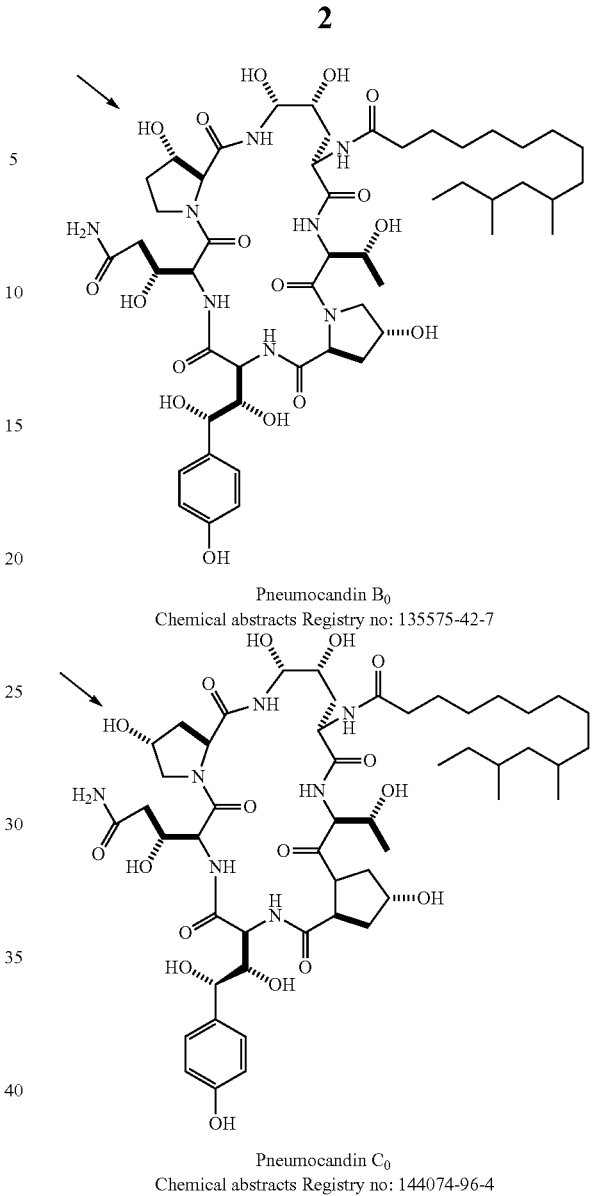

Pneumocandin $B_0$
Chemical abstracts Registry no: 135575-42-7

Pneumocandin $C_0$
Chemical abstracts Registry no: 144074-96-4

Several methods for detection of Pneumocandins are known. They are however generally cumbersome and inefficient for selective detection of Pneumocandin $B_0$ or selective detection of Pneumocandin $C_0$. E.g., crystallization and reverse phase chromatography have been unable to separate Pneumocandin $B_0$ from Pneumocandin $C_0$. Normal phase chromatography utilizing ethyl acetate/methanol/water mobile phases is able to separate Pneumocandin $B_0$ from Pneumocandin $C_0$. This method, however, suffers from low Pneumocandin solubility in the loading solution and also from somewhat bad robustness. In addition, this mobile phase is not very compatible with mass spectrometric methods, which limits the usefulness of the method for analytical purposes.

RELEVANT PRIOR ART

J Mass Spectrom. 2007 April; 42(4):440-9 by Rochat et al. Detection of Caspofungin by LC-MS/MS in plasma.
Rapid Commun Mass Spectrom. 2004; 18(23):2871-7 by Egle et al. Double column-switching technique (LC-LC)

for liquid chromatography/electrospray ionisation tandem mass spectrometry for fully automated analysis of Caspofungin.

J Chromatogr B Analyt Technol Biomed Life Sci. 2008 Sep. 1; 872(1-2): 1-22. Epub 2008 Jul. 26. Quantitative bioanalysis of peptides by liquid chromatography coupled to (tandem) mass spectrometry Journal of mass spectrometry: JMS, (1999 July) Vol. 34, No. 7, pp. 733-40 by Qin et al. Collision-induced dissociation of protonated MK-0991: novel ring opening of a cyclic hexapeptide in the gas phase.

The following abbreviations are used with the specified meaning throughout this specification:

ABBREVIATIONS

API—Active Pharmaceutical Ingredient(s)
MS—Mass Spectrometry
MS/MS—Tandem Mass Spectrometry
LC—Liquid Chromatography
ACN—Acetonitrile
AmAc—Ammonium Acetate
HILIC—Hydrophilic Interaction Liquid Chromatography
HPLC—High Performance Liquid Chromatography
Q—Quadrupole
TOF—Time of Flight
CE—Collision energy

SUMMARY OF THE INVENTION

This invention concerns specific detection of Pneumocandin $B_0$ and/or specific detection of Pneumocandin $C_0$ by mass spectrometry (MS). The invention is based on the surprising discovery of different fragmentation behaviour of $B_0$ compared to $C_0$.

The invention can be utilized for detecting these molecules specifically. It can also be used for monitoring the presence of these molecules in a sample, or in an industrial process. Thus, even when Pneumocandin $B_0$ and $C_0$ are not chromatographically separated, a skilled artisan can analyze the content of the often desired $B_0$ compound during a manufacturing process. Simultaneously or alternatively, the content of the seldom desired $C_0$ compound can be analyzed during a manufacturing process. Knowledge and documentation of the content of these compounds is important for any commercial or scientific production of Pneumocandin $B_0$ or Pneumocandin $C_0$.

DETAILED DESCRIPTION OF THE INVENTION

Figure 1A:
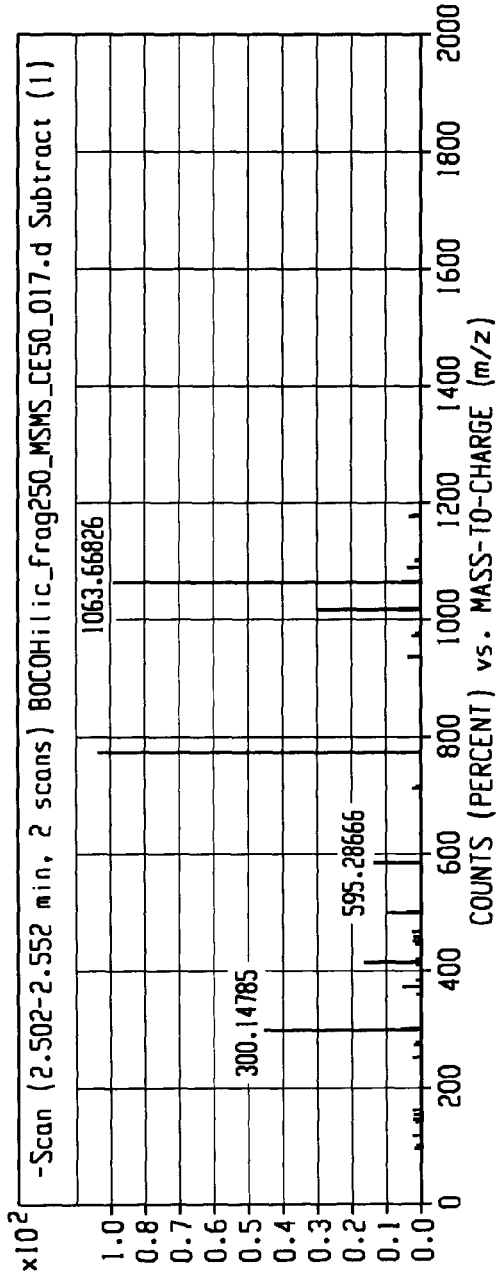
FIG. 1. Mass spectra from an LC-MS/MS-experiment on a sample containing both Pneumocandin $B_0$ and Pneumocandin $C_0$. Deprotonated Pneumocandin $B_0$ (A) or Pneumocandin $C_0$ (B) was isolated at m/z 1063 in the quadrupole (Q). The isolated pseudo-molecular ion was then fragmented in the collision cell at collision energy 50 V. The TOF analyzer was set to scan between m/z 100-2200. (A) Mass spectrum of Pneumocandin $B_0$ where a specific fragment at m/z 300 was found. (B) Mass spectrum of Pneumocandin $C_0$ where a nearly specific fragment at m/z 356 was found.

The detection of Pneumocandins may be performed with UV detection. For analytical purposes, an MS-detector capable of performing MS/MS is more preferably used. The inventors of the present invention surprisingly found, by performing MS/MS in both positive and negative ion mode, that Pneumocandin $B_0$ and Pneumocandin $C_0$ fragments differently when the deprotonated molecular ion ([M−H]−) is chosen for MS/MS. Notably, fragment ions can be found which are specific for (i.e. that the fragment ion exclusively occurs only for one of the isomers) or nearly specific for (i.e. that the fragment ion occurs in much higher abundance for one of the isomers) Pneumocandin $B_0$ and Pneumocandin $C_0$, respectively. For Pneumocandin $B_0$, these ions have m/z-values of e.g. 300, 416 and 452. For Pneumocandin $C_0$, these ions have m/z-values of e.g. 338, 356 and 360.

By combining chromatographic separation with monitoring of those specific fragments (preferable using LC-MS/MS-technology) for Pneumocandin $B_0$ and Pneumocandin $C_0$, it is possible to detect and quantify Pneumocandin $B_0$ and Pneumocandin $C_0$ in complex fermentate samples.

Authentic reference standards for Pneumocandin $B_0$ and Pneumocandin $C_0$ must be included in connection to the analysis. The identity of the respective isomer in the sample is determined from comparison of retention times and specific fragments with the authentic reference standards. The quantifications of Pneumocandin $B_0$ and Pneumocandin $C_0$ are performed from area comparison with the authentic reference standards (using calibration curves), as the area of the respective isomer peak is proportional to the amount of the respective isomer.

To be able to create an analytical method to analyze the content of $B_0$ and $C_0$ in a sample it was necessary to either separate the two compounds chromatographically or find compound specific ions, qualifiers or MS/MS-transitions. Since neither of the $B_0$ or $C_0$ standards supplied were pure enough, we had to develop a fast separation of $B_0$ or $C_0$ before further MS-experiments could be done. Since reverse phase chromatography did not show any promising results, it was decided to try and set up a method based on normal phase chromatography. Initial testing was done on an Agilent-$NH_2$ column, with different combinations of Acetonitrile (ACN) and 0, 1% Ammonium Acetate solution in water (AmAc) which showed signs of separation but the resolution was far from good enough to give a base line separation of the two compounds. An Ascentis Express HILIC column, from Sigma-Aldrich was then tested based on that it is a "normal phase" type of column and that the Fused-Core particle technology is known to give good resolution. After testing out different combinations of ACN and AmAc a mixture of 85/15 (ACN/AmAc) was chosen. The result was a baseline separation of $B_0$ and $C_0$. Increasing the ACN content gave longer retention times but broader peaks, and increasing the AmAc content gave shorter retention times but less separation. $B_0$ and $C_0$ were monitored with ESI/MS in positive mode.

Q-TOF fragmentation with collision energies ranging from 10-60 V did not result in specific fragments on the pseudo-molecular ion $[M+H]^+$ or on the sodium adduct $[M+Na]^+$. However, negative ionization with collision energies ranging from 10-60 V surprisingly revealed specific or nearly specific $B_0$-fragments despite its minor difference from $C_0$.

The invention is defined by the claims and not by the following illustrative examples:

EXAMPLES

Example I

In this experiment, an Agilent 1200 HPLC system coupled to an Agilent 6520 Quadrupole Time-of-Flight (Q-TOF) mass spectrometer was used. The Agilent 1200 HPLC system consisted of a binary pump, degasser, thermostated autosampler and a thermostated column compartment (set to 25° C.). A Supelco Ascentis Express HILIC 15 cm×4.6 mm, 2.7 μm column was used. The mobile phase consisted of 15% v/v 0.1% w/w ammonium acetate pH 4.5 and 85% v/v ACN. The flow rate was 1 ml/min. The MS ion source parameters were as follows: Nebuliser pressure 50 psig, drying gas flow 10 l/min, drying gas temp 350° C., capillary exit voltage 250V. LC-MS/MS was performed in the negative ion mode were deprotonated Pneumocandin $B_0$ or Pneumocandin $C_0$ were isolated at m/z 1063 in the quadrupole (Q). The isolated pseudo-molecular ion was then fragmented in the collision cell at collision energy 50 V. The TOF analyzer was then set to scan between m/z 100-2200 (FIG. 1A-B) or to monitor selected ions (FIG. 2A-C).

Figure 1B:
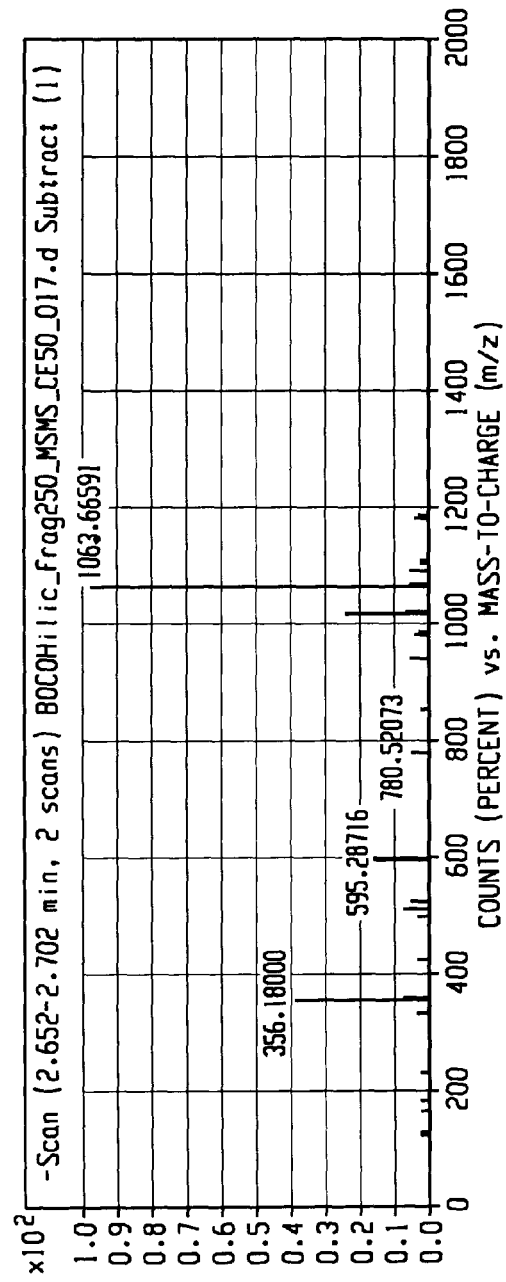

FIG. 1A shows the mass spectrum of Pneumocandin $B_0$ (from a sample containing both Pneumocandin $B_0$ and Pneumocandin $C_0$) where a specific fragment at m/z 300 was found. FIG. 1B shows the mass spectrum of Pneumocandin $C_0$ (from a sample containing both Pneumocandin $B_0$ and Pneumocandin $C_0$) where a nearly specific fragment at m/z 356 was found.

Figure 2A:
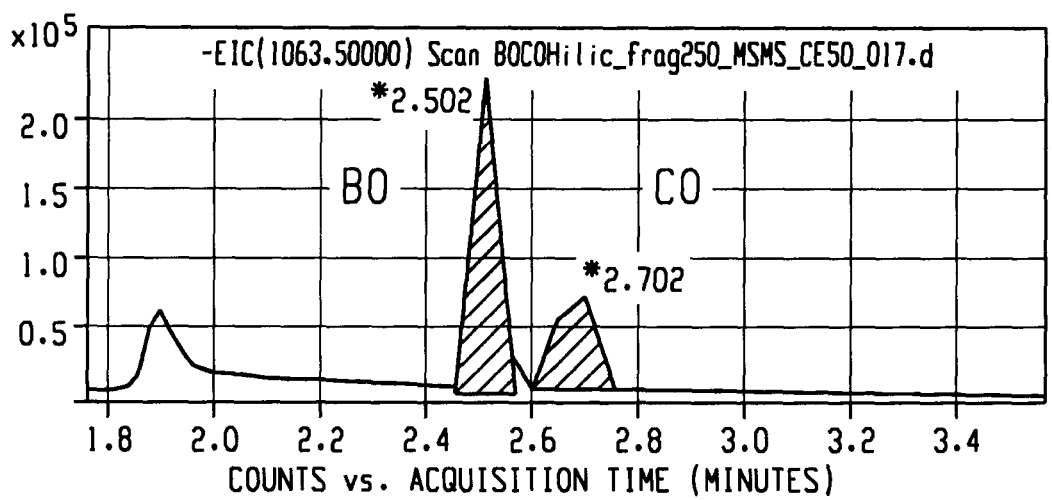
FIG. 2. Mass chromatograms from an LC-MS/MS-experiment on a sample containing both Pneumocandin $B_0$ and Pneumocandin $C_0$. Deprotonated Pneumocandin $B_0$ or Pneumocandin $C_0$ was isolated at m/z 1063 in the quadrupole (Q). The isolated pseudo-molecular ion was then fragmented in the collision cell at collision energy 50 V. The TOF analyzer was set to monitor selected ions. (A) Chromatographic separation of Pneumocandin $B_0$ from Pneumocandin $C_0$ in a sample containing both isomers. (B) The combined power of chromatographic separation and MS/MS-detection of the fragment at m/z 300 that is specific for Pneumocandin $B_0$. (C) The combined power of chromatographic separation and MS/MS-detection of the fragment at m/z 356 that nearly is specific for Pneumocandin $C_0$.
Figure 2B:
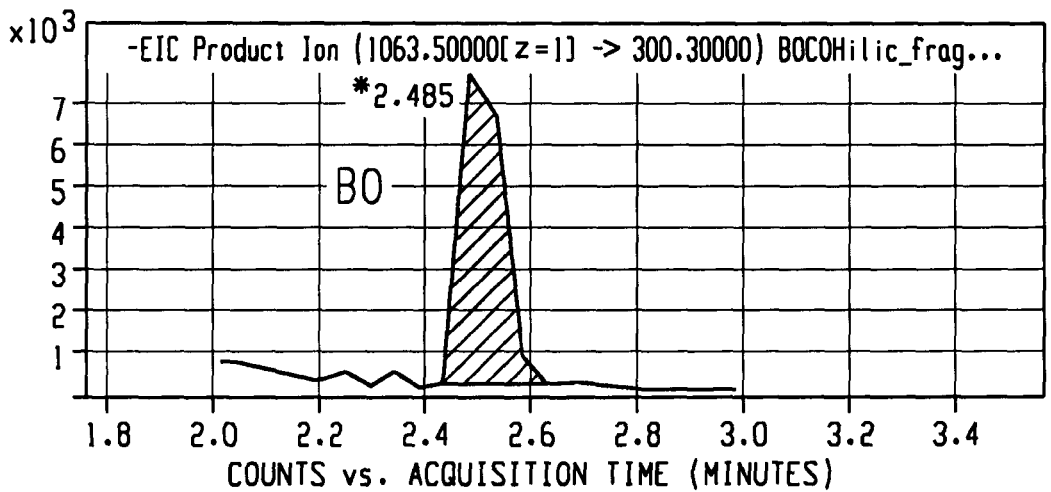
Figure 2C:
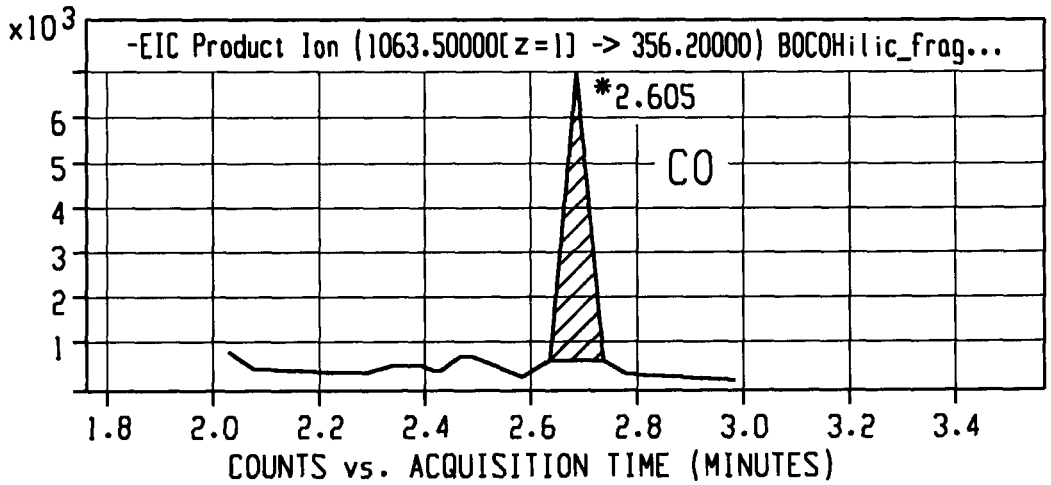

FIG. 2A shows that this chromatographic set-up is able to separate Pneumocandin $B_0$ from Pneumocandin $C_0$ in a sample containing both isomers. FIG. 2B shows the combined power of chromatographic separation and MS/MS-detection of the fragment at m/z 300 that is specific for Pneumocandin $B_0$. FIG. 2C shows the combined power of chromatographic separation and MS/MS-detection of the fragment at m/z 356 that nearly is specific for Pneumocandin $C_0$.

Example II

In this experiment, a Thermo Fisher Surveyor HPLC system coupled to a Thermo Fisher LXQ linear ion trap mass spectrometer was used. The Surveyor HPLC system consisted of a quaternary pump, degasser, thermostated autosampler and a thermostated column compartment (set to 40° C.). A Supelco Ascentis Si HILIC 15 cm×2.1 mm, 5 μm column was used. The mobile phase consisted of 13% v/v 0.1% w/w ammonium acetate pH 4.5 and 87% v/v ACN. The flow rate was 0.2 ml/min. The MS ion source parameters were as follows: sheath gas 35 (arbitrary units), auxiliary gas 15 (arbitrary units), capillary temperature 350° C., spray voltage kV. LC-MS/MS was performed in the negative ion mode were deprotonated Pneumocandin $B_0$ or Pneumocandin $C_0$ were isolated (at m/z 1063) and fragmented (at collision energy 13) in the ion trap. The ion trap was set to scan between m/z 290-1100 (FIG. 3A-E) or to monitor selected ions (FIG. 4A-C).

Figure 3A:
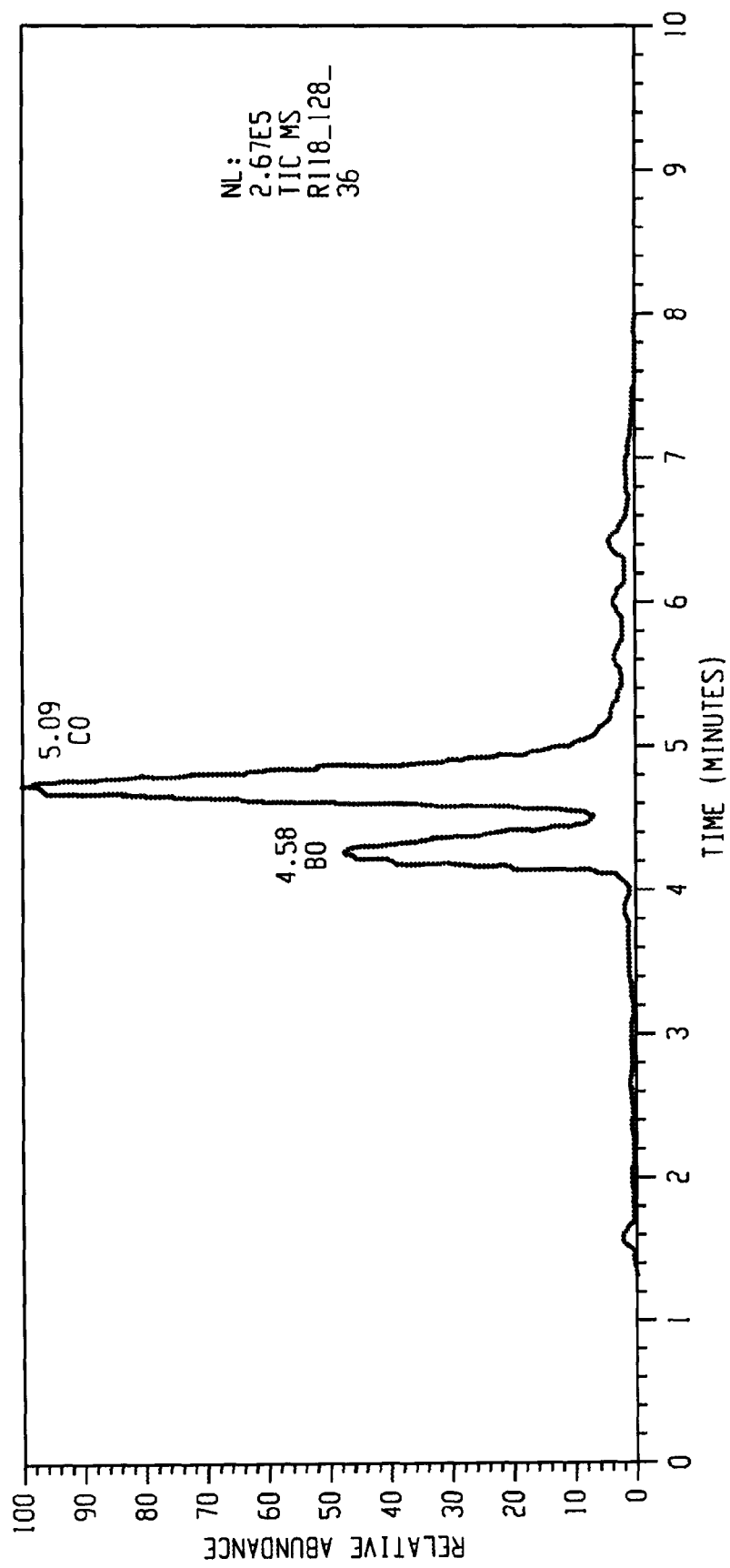
FIG. 3. TIC chromatogram and mass spectra from an LC-MS/MS-experiment on a sample containing both Pneumocandin $B_0$ and Pneumocandin $C_0$. Deprotonated Pneumocandin $B_0$ or Pneumocandin $C_0$ were isolated (at m/z 1063) and fragmented (at collision energy 13) in the ion trap. The ion trap was set to scan between m/z 290-1100. (A) Chromatographic separation of Pneumocandin $B_0$ from Pneumocandin $C_0$ in a sample containing both isomers. (B) Mass spectrum of Pneumocandin $B_0$ where specific fragments at m/z 300, 416 and 452 were found. (C) Mass spectrum of Pneumocandin $C_0$ where specific fragments at m/z 338 and 360 were found. (D) Close-up of 3B. (E) Close-up of 3C.
Figure 3B:
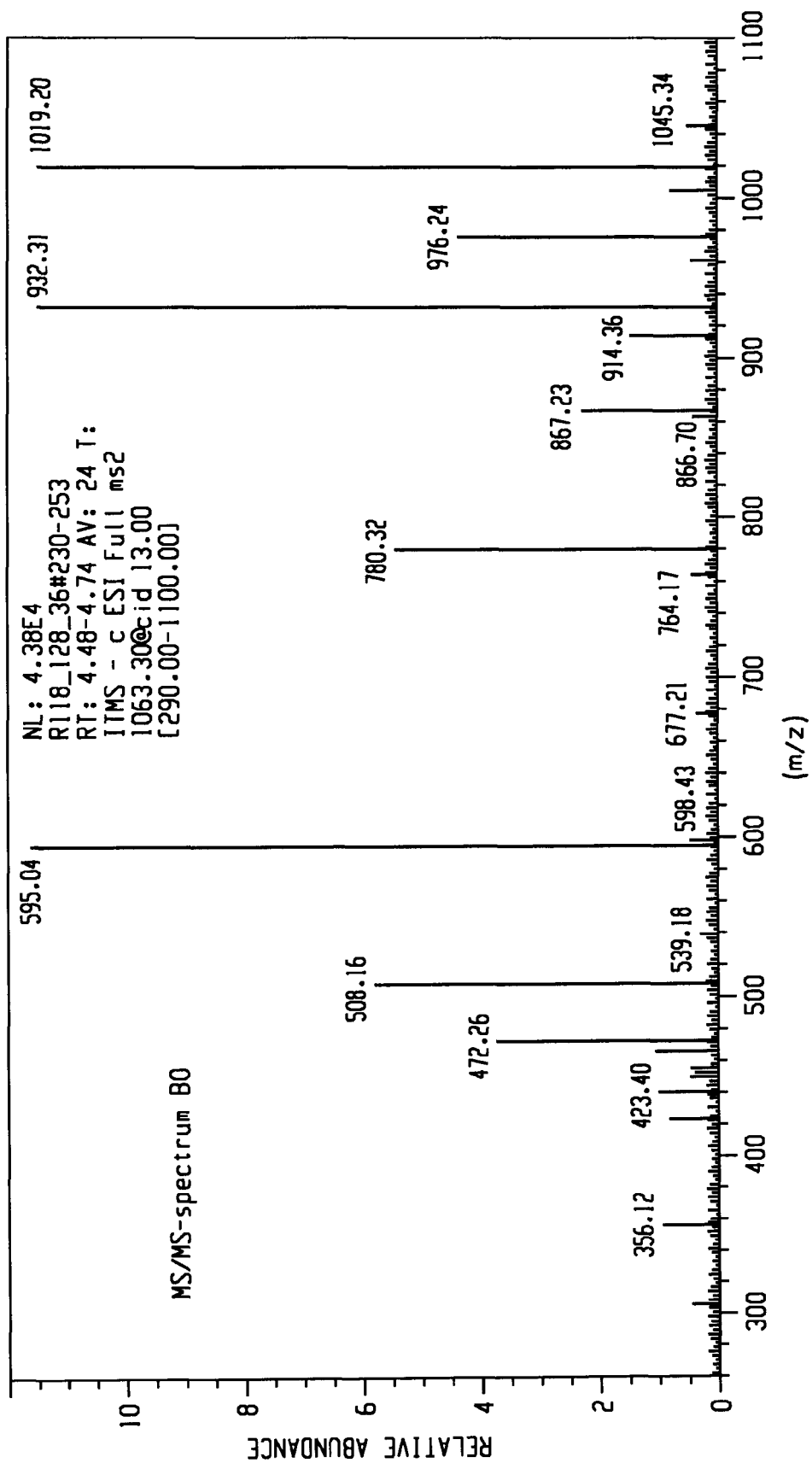
Figure 3C:
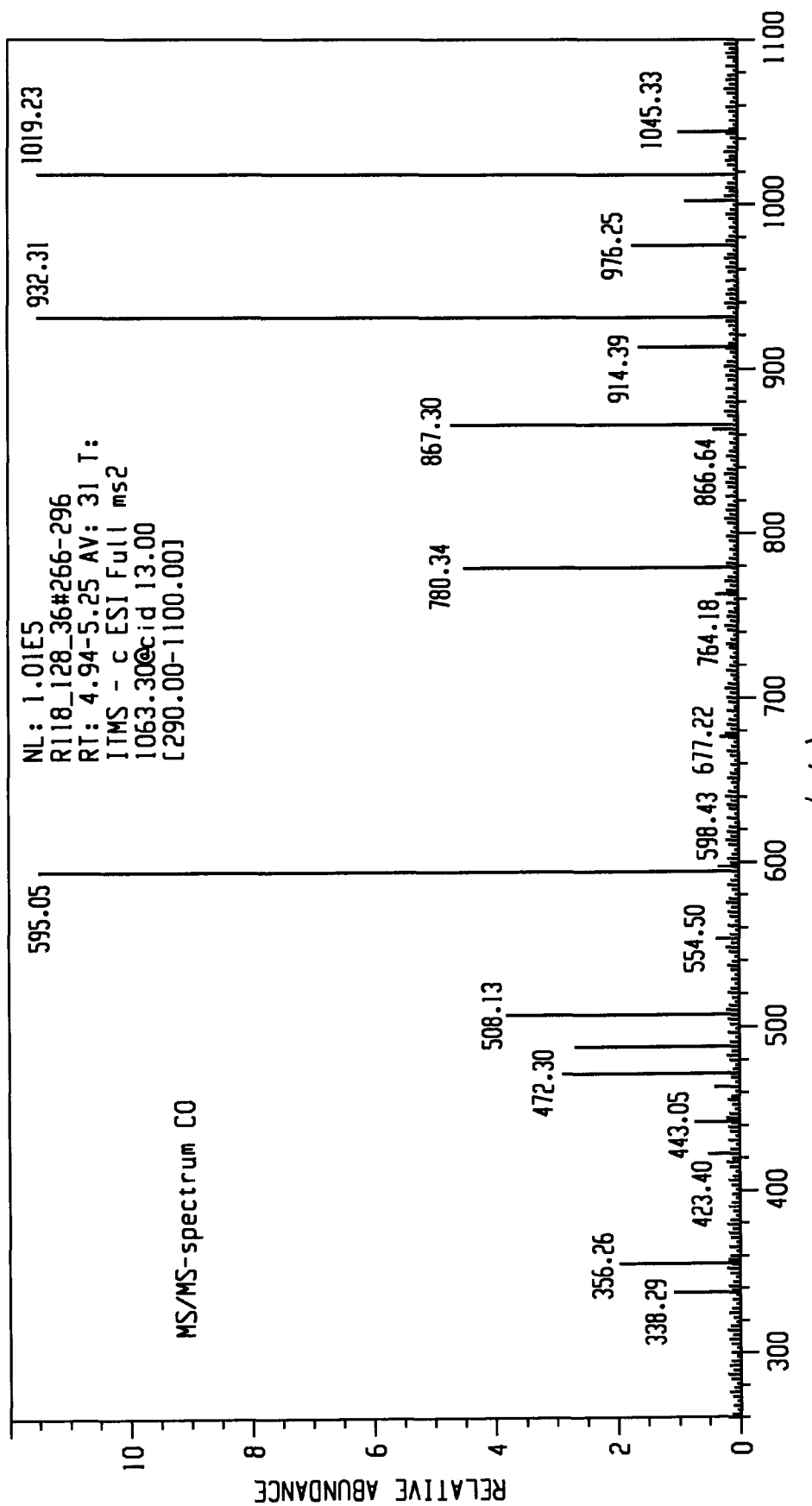
Figure 3D:
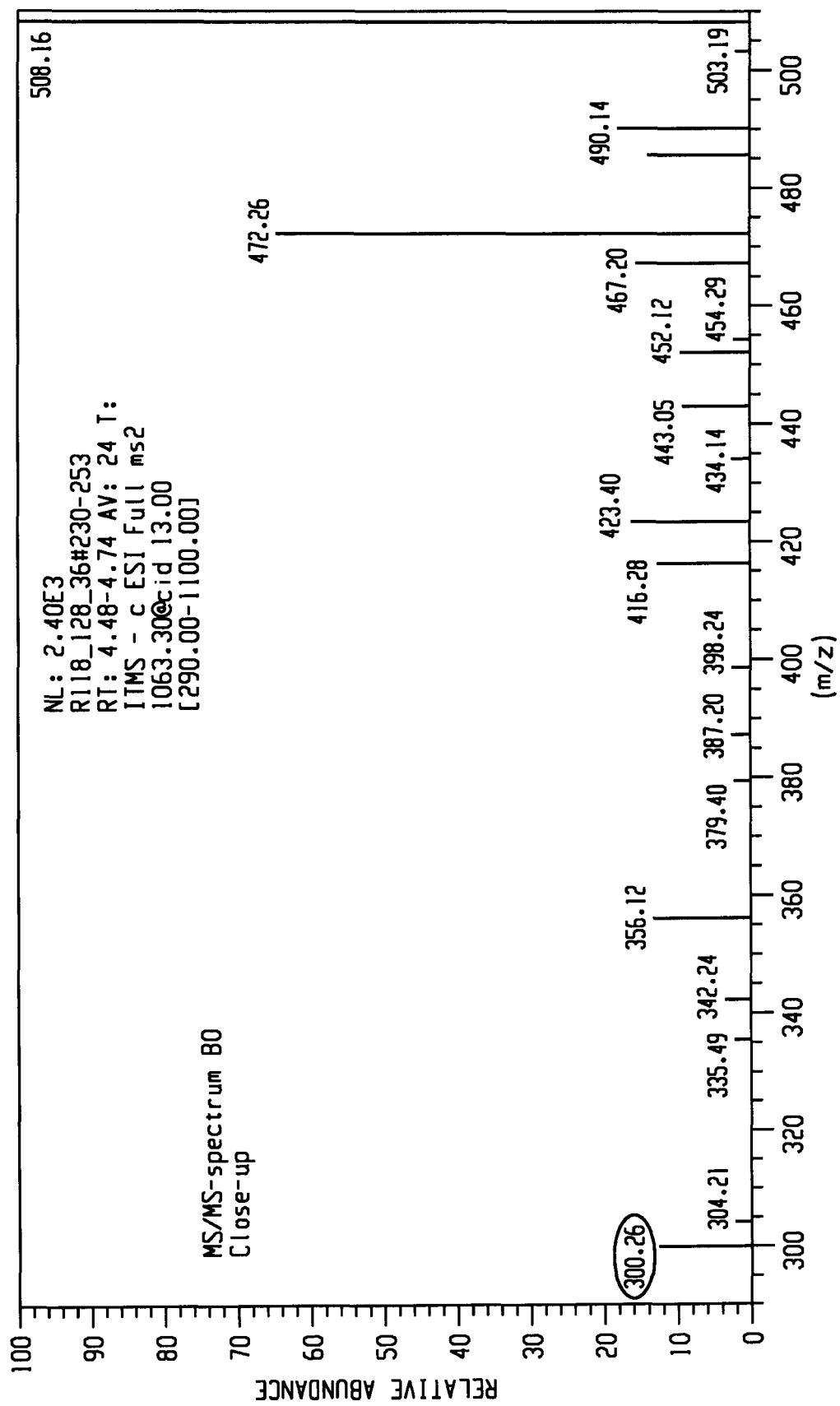
Figure 3E:
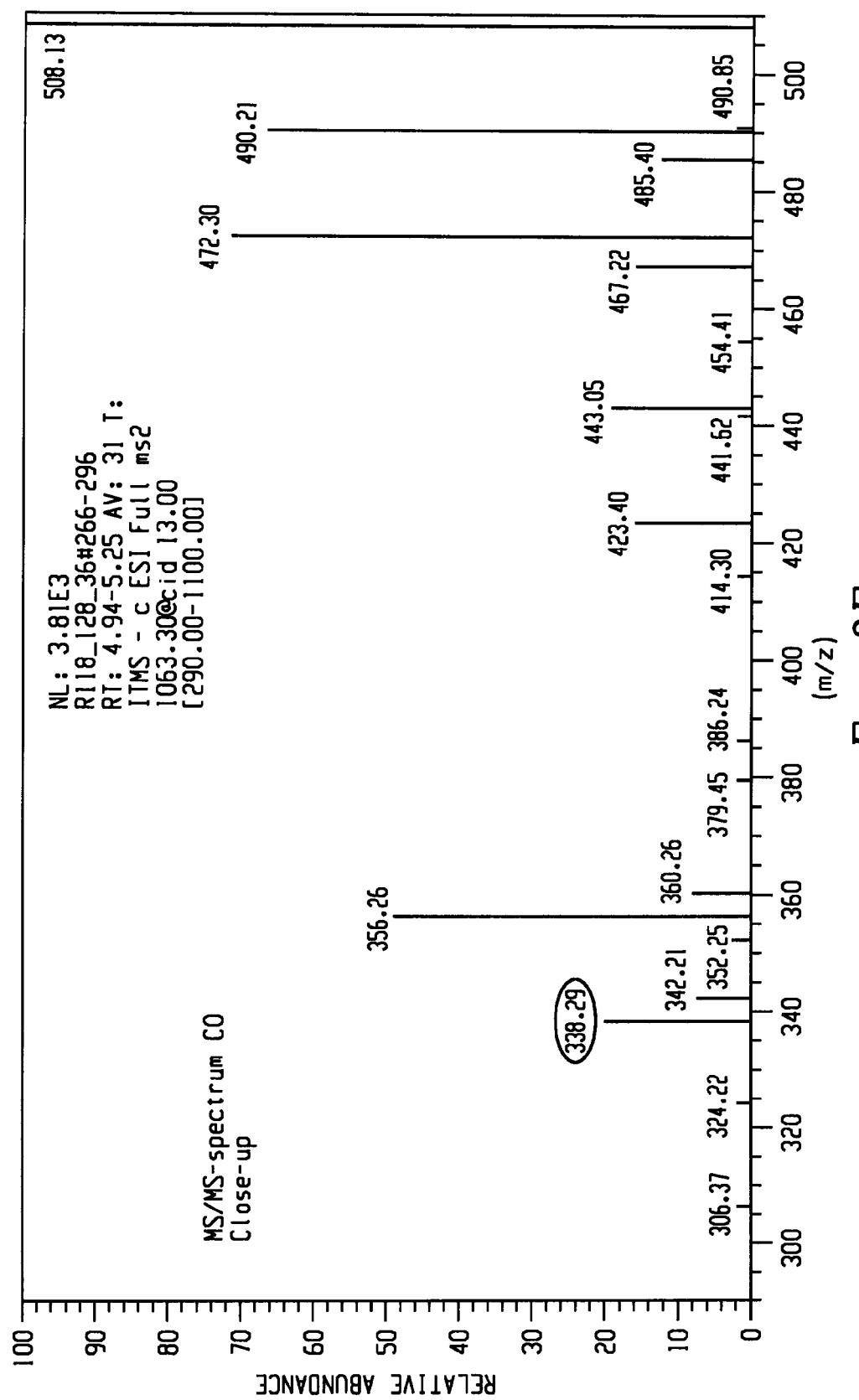
Figure 4A:
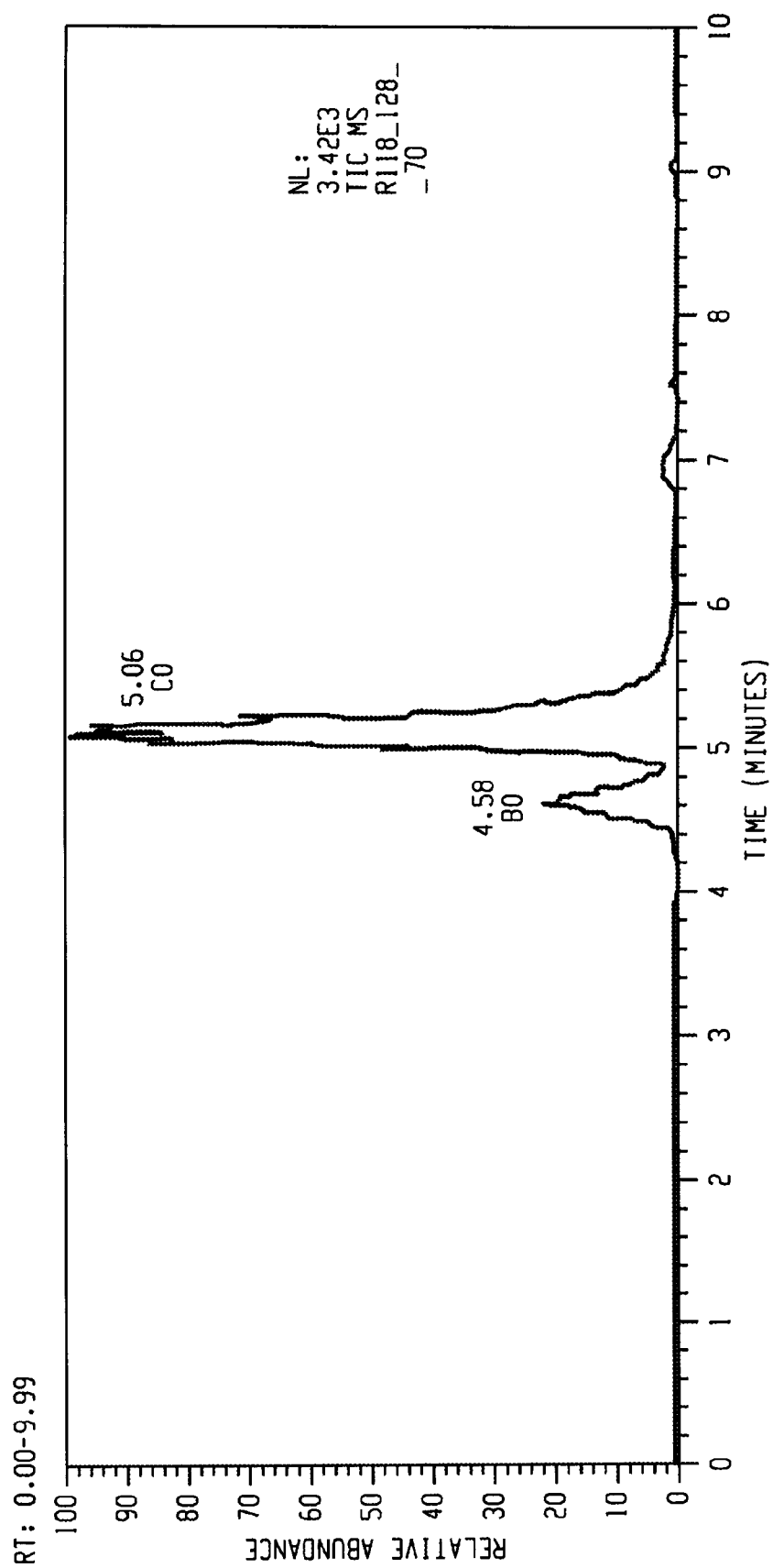
FIG. 4. Mass chromatograms from an LC-MS/MS-experiment on a sample containing both Pneumocandin $B_0$ and Pneumocandin $C_0$. Deprotonated Pneumocandin $B_0$ or Pneumocandin $C_0$ were isolated (at m/z 1063) and fragmented (at collision energy 13) in the ion trap. The ion trap was set to monitor selected ions. (A) Chromatographic separation of Pneumocandin $B_0$ from Pneumocandin $C_0$ in a sample containing both isomers. (B) The combined power of chromatographic separation and MS/MS-detection of the fragment at m/z 300 that is specific for Pneumocandin $B_0$. (C) The combined power of chromatographic separation and MS/MS-detection of the fragment at m/z 338 that is specific for Pneumocandin $C_0$.
Figure 4B:
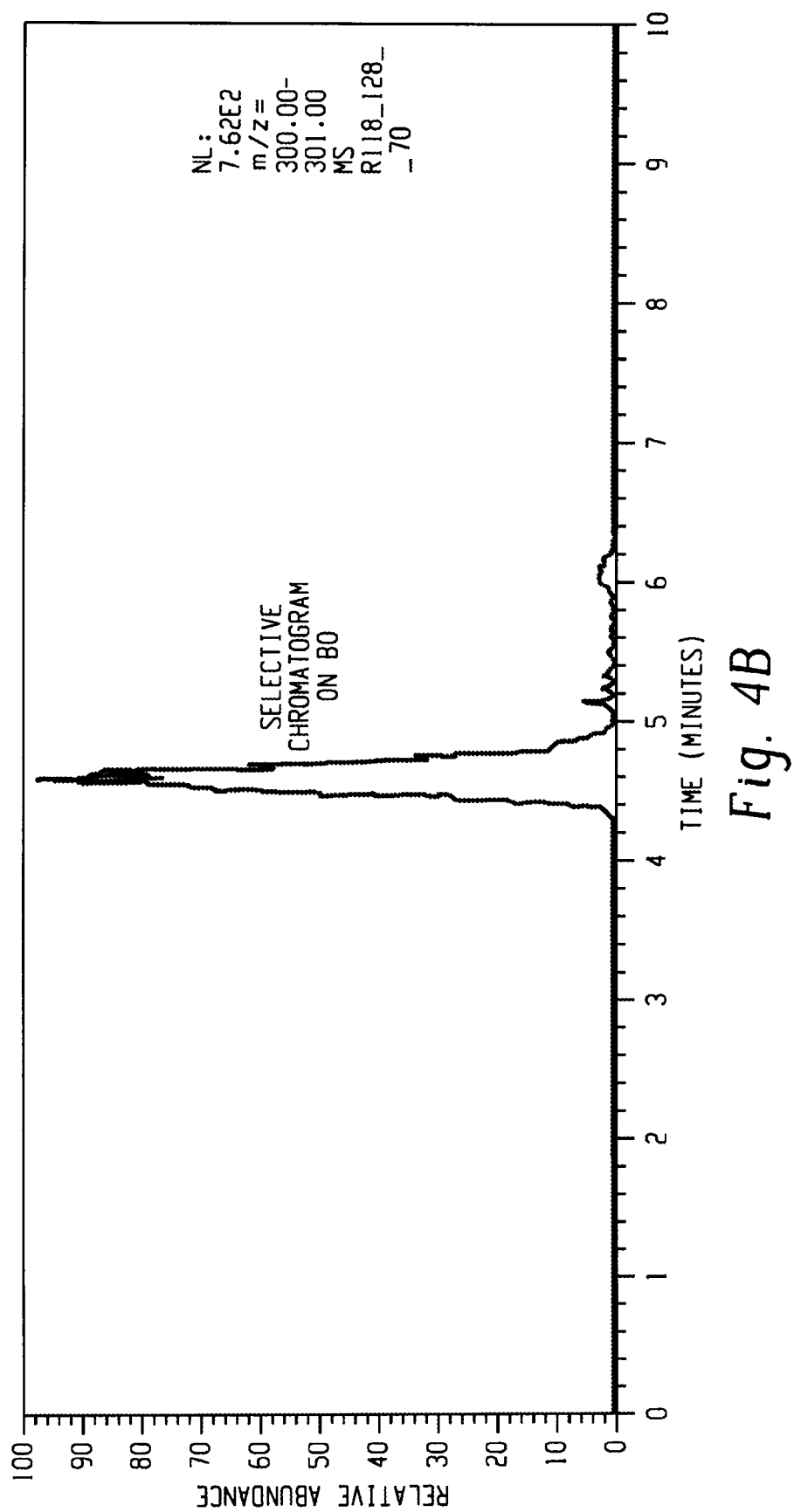
Figure 4C:
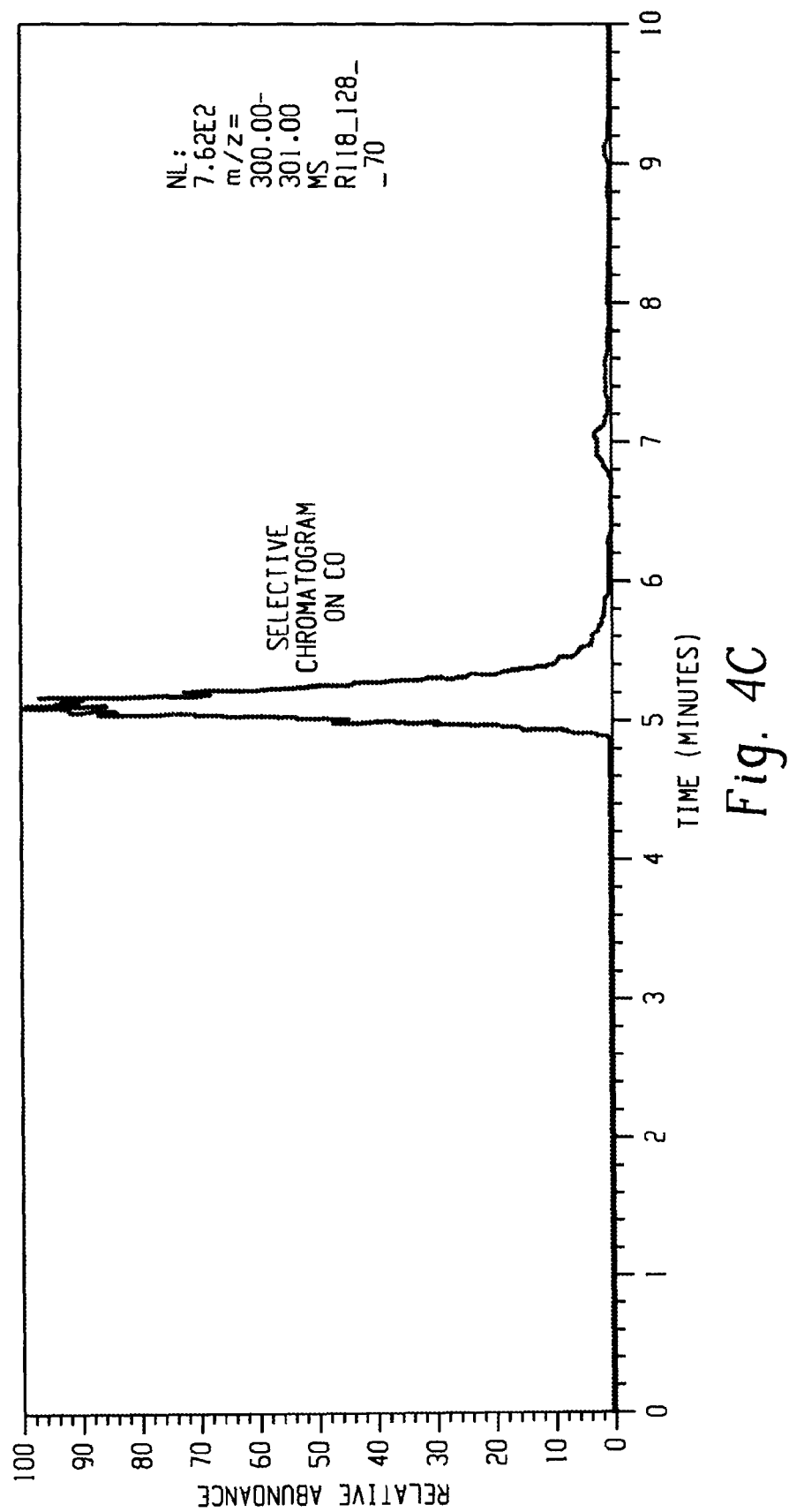
Figure 5C:
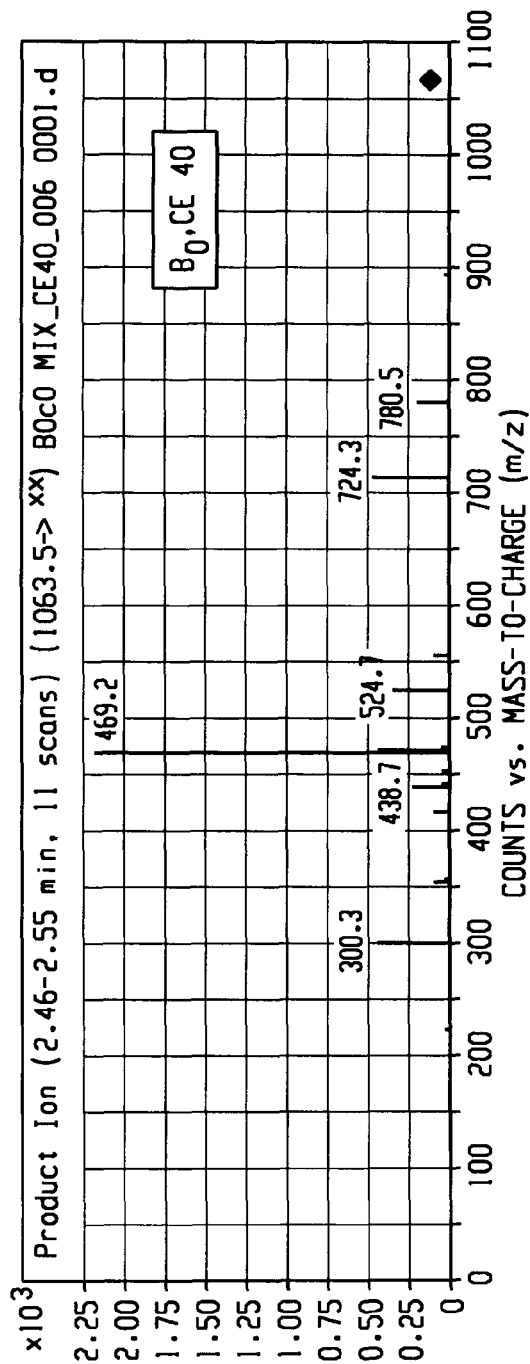
FIG. 5. Mass spectra from an LC-MS/MS-experiment on a sample containing both Pneumocandin $B_0$ and Pneumocandin $C_0$. Deprotonated Pneumocandin $B_0$ (A, C, E, G, I and K) or Pneumocandin $C_0$ (B, D, F, H, J and L) were isolated at m/z 1063 in the first quadrupole (Q). The isolated pseudo-molecular ion was then fragmented in the second quadrupole (Q) at collision energy 35 V (A and B), 40 V (C and D), 45 V (E and F), 50 V (G and H), 55 (I and J) and 60 V (K and L). The third quadrupole (Q) was then set to scan between m/z 60-1100. At each collision energy, specific fragments for Pneumocandin $B_0$ and Pneumocandin $C_0$ can be found. Some of these specific fragments appear over a broad range of collision energies, while others are restricted to a smaller range. See text for more details.
Figure 5D:
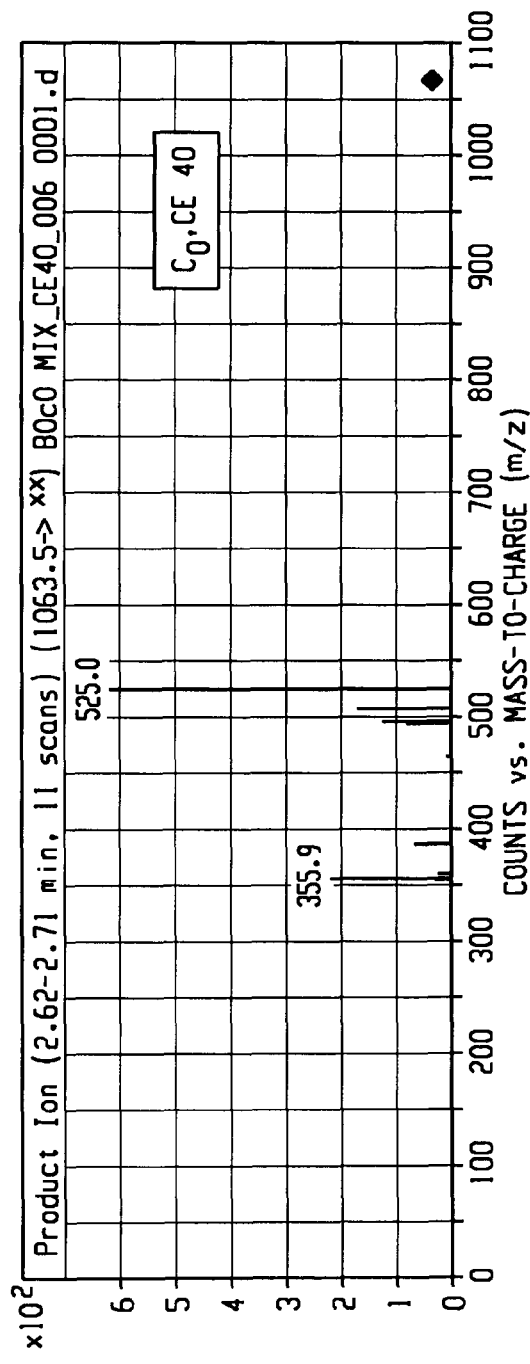
Figure 5E:
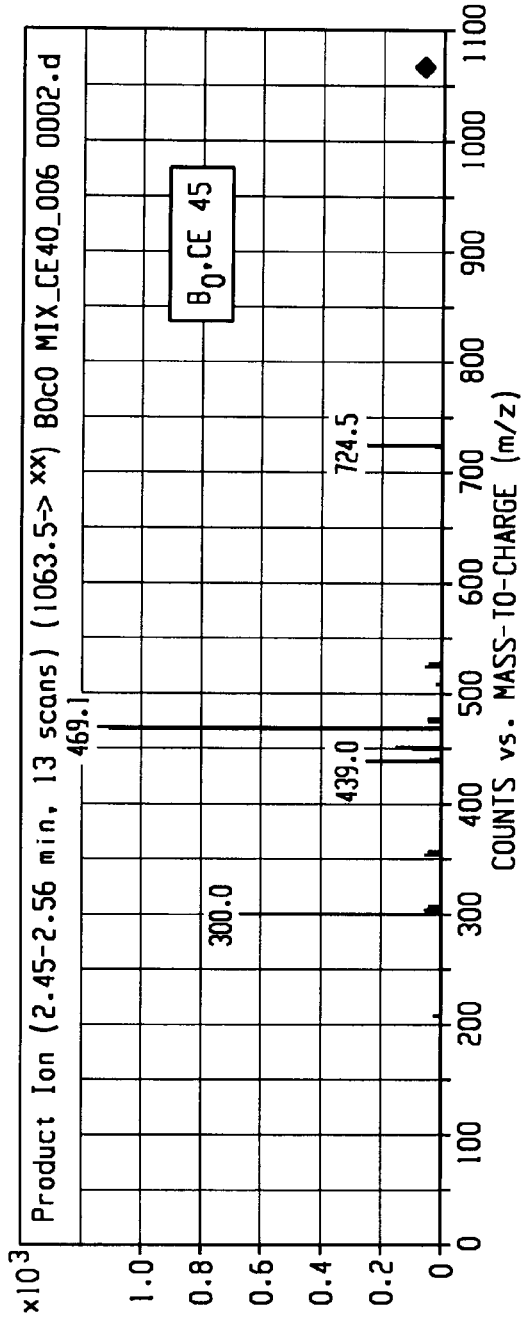
Figure 5F:
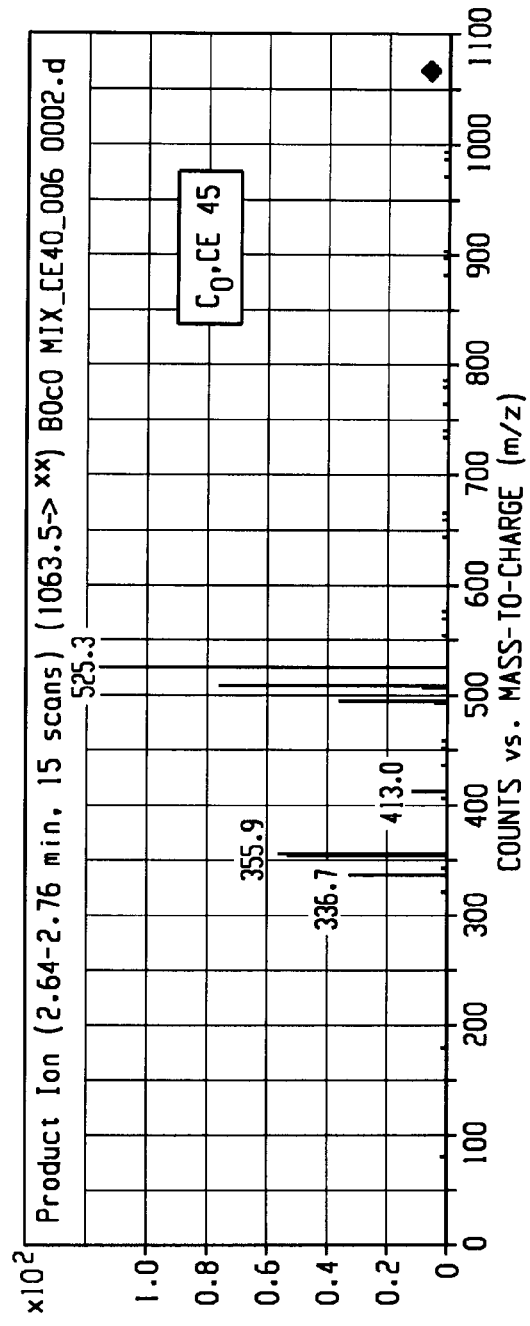
Figure 5G:
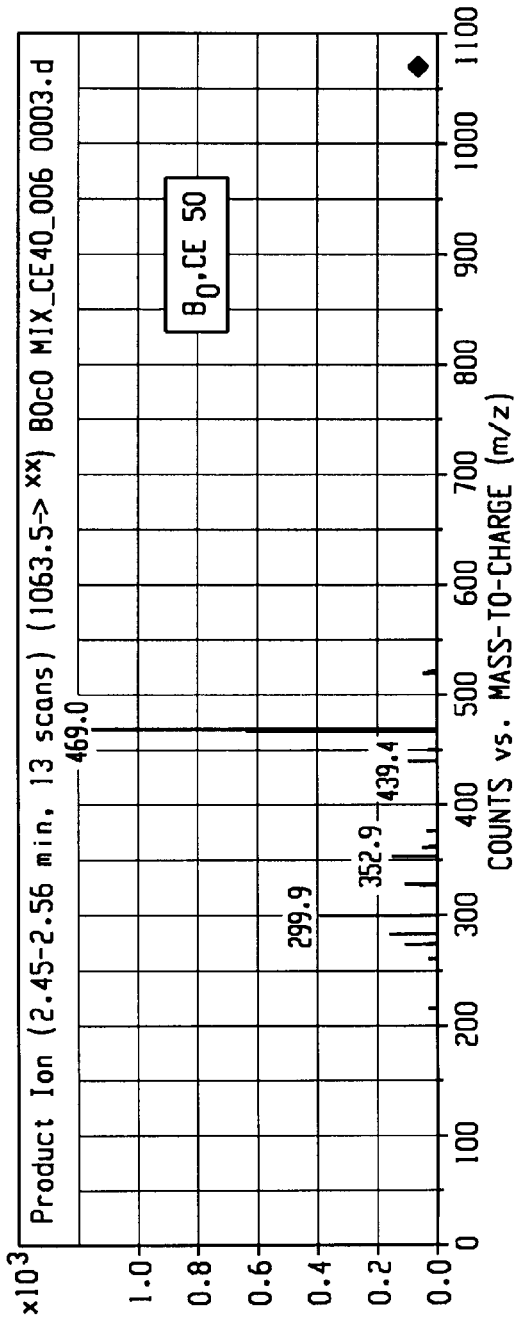
Figure 5H:
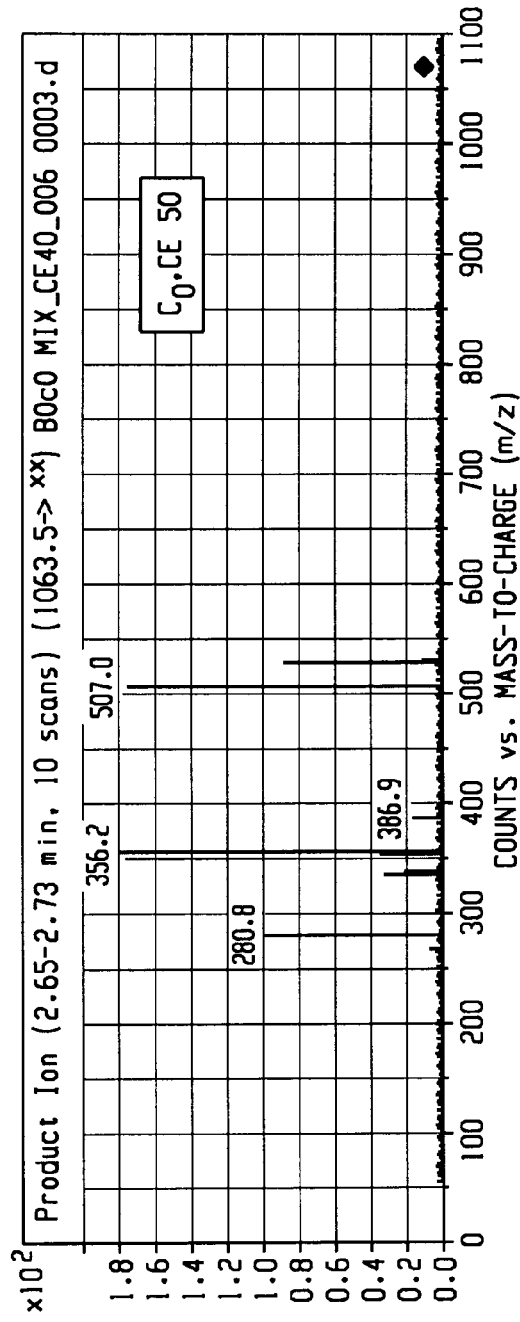
Figure 5I:
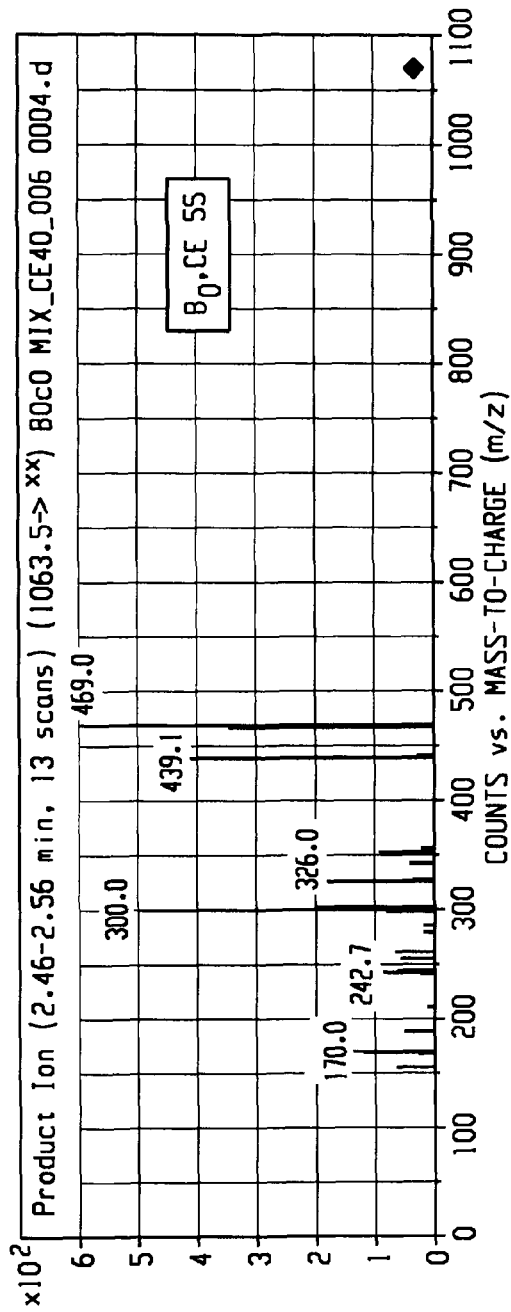
Figure 5J:
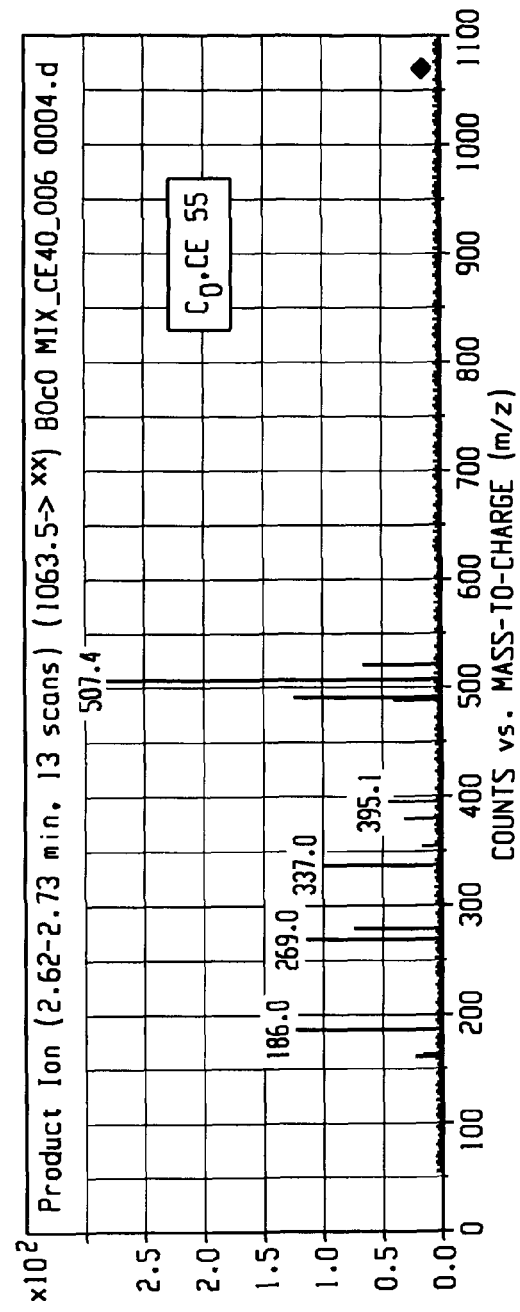
Figure 5K:
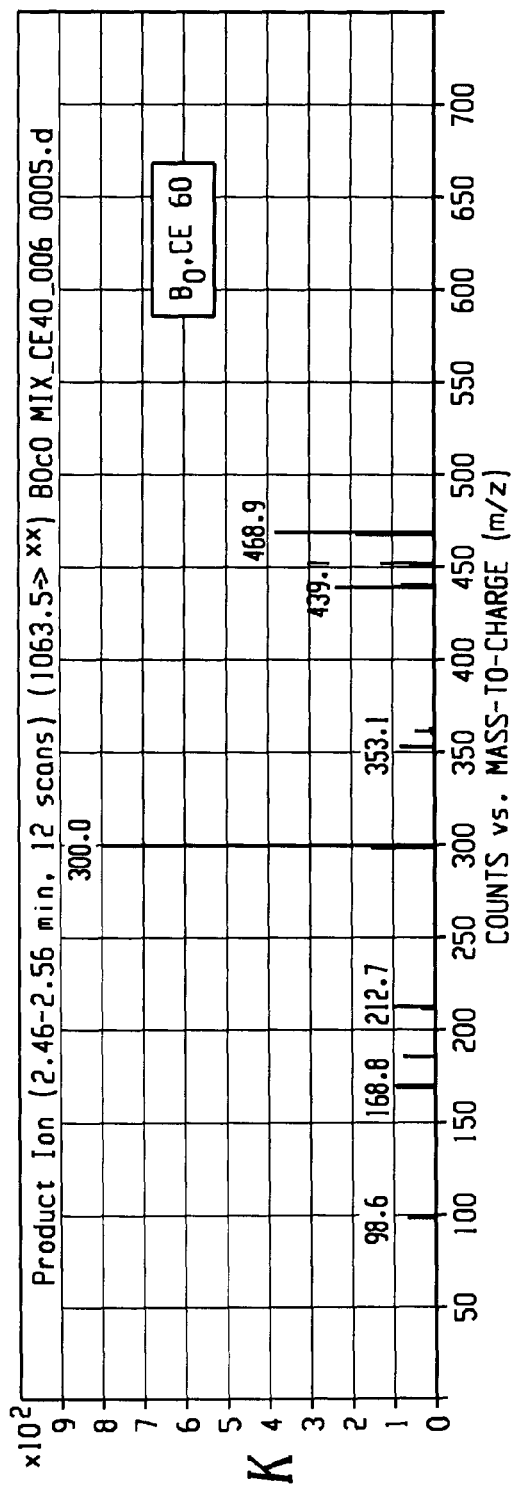
Figure 5L:
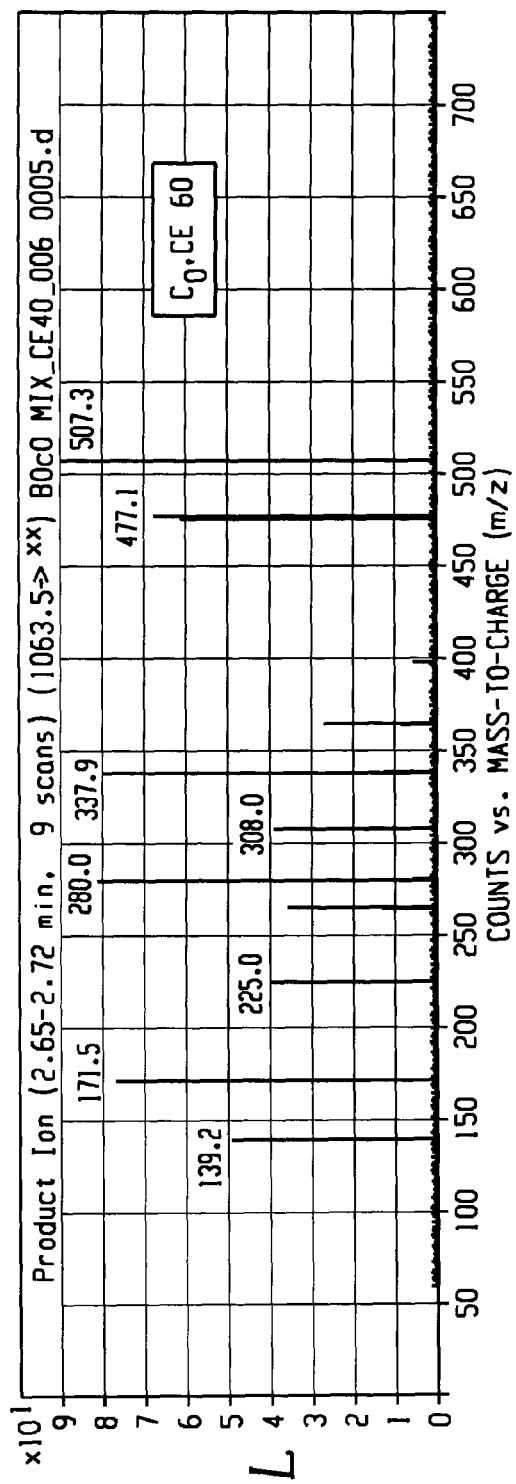

FIG. 3A shows that this chromatographic set-up is able to separate Pneumocandin $B_0$ from Pneumocandin $C_0$ in a sample containing both isomers. FIGS. 3B and 3D (close-up of 3B) show the mass spectrum of Pneumocandin $B_0$ (extracted from the experiment shown in FIG. 3A) where specific fragments at m/z 300, 416 and 452 were found. FIGS. 3C and 3E (close-up of 3C) show the mass spectrum of Pneumocandin $C_0$ (extracted from the experiment shown in FIG. 3A) where specific fragments at m/z 338 and 360 were found. FIG. 4A shows that this chromatographic set-up is able to separate Pneumocandin $B_0$ from Pneumocandin $C_0$ in a sample containing both isomers. FIG. 4B shows the combined power of chromatographic separation and MS/MS-detection of the fragment at m/z 300 that is specific for Pneumocandin $B_0$. FIG. 4C shows the combined power of chromatographic separation and MS/MS-detection of the fragment at m/z 338 that is specific for Pneumocandin $C_0$.

Example III

In this experiment, an Agilent 1200 HPLC system coupled to an Agilent 6410 Triple Quadrupole (QQQ) mass spectrometer was used. The Agilent 1200 HPLC system consisted of a binary pump, degasser, thermostated autosampler and a thermostated column compartment (set to 25° C.). A Supelco Ascentis Express HILIC 15 cm×4.6 mm, 2.7 μM column was used. The mobile phase consisted of 15% v/v 0.1% w/w ammonium acetate pH 4.5 and 85% v/v ACN. The flow rate was 1 mL/min. The MS ion source parameters were as follows: Nebuliser pressure 50 psig, drying gas flow 10 l/min, drying gas temp 325° C., capillary exit voltage 4000 V. LC- MS/MS was performed in the negative ion mode were deprotonated Pneumocandin $B_0$ or Pneumocandin $C_0$ were isolated at m/z 1063 in the first quadrupole (Q). The isolated pseudo-molecular ion was then fragmented in the second quadrupole/collision cell (Q) at collision energy 35-60 V. The third quadrupole (Q) was then set to scan between m/z 60-1100.

FIG. 5A-L show the corresponding mass spectra of Pneumocandin $B_0$ and Pneumocandin $C_0$ (from a sample containing both Pneumocandin $B_0$ and Pneumocandin $C_0$) at collision energies 35-60 V. These figures show that at each collision energy, specific fragments for Pneumocandin $B_0$ and Pneumocandin $C_0$ can be found. Some of these specific fragments appear over a broad range of collision energies, while others are restricted to a smaller range. Some examples of specific fragments for Pneumocandin $B_0$ are m/z 300, 439 and 469 at collision energies 35-60 V, m/z 724 at collision energies 35-45 V and m/z 326 at collision energy 55 V. Some examples of specific fragments for Pneumocandin $C_0$ are m/z 507 at collision energies 45-60 V and m/z 139, 280 and 338 at collision energy 60 V.

The invention claimed is:

1. Method of detecting Pneumocandin $B_0$ and/or Pneumocandin $C_0$, in a sample comprising,
   providing a sample containing, or at least suspected of containing, Pneumocandin $B_0$ together with Pneumocandin $C_0$
   providing a MS reference standard for Pneumocandin $B_0$ and Pneumocandin $C_0$
   performing MS, in negative mode, of the sample, the MS adapted to produce Pneumocandin $B_0$ specific fragments and/or Pneumocandin $C_0$ specific fragments,
   determining the presence, or lack thereof, of Pneumocandin $B_0$ specific fragments and/or Pneumocandin $C_0$ specific fragments by comparison of the MS results of the sample against the standard.

2. The method of claim 1, wherein the specific fragments for Pneumocandin $B_0$ is approximately m/z 300, 439 or 469.

3. The method of claim 2, wherein the collision energies is approximately 35-60 V.

4. The method of claim 1, wherein the specific fragments for Pneumocandin $B_0$ is approximately m/z 724.

5. The method of claim 4, wherein the collision energy is approximately 35-45 V.

6. The method of claim 1, wherein the specific fragments for Pneumocandin $B_0$ is approximately m/z 326.

7. The method of claim 6, wherein the collision energy is approximately 55 V.

8. The method of claim 1, wherein the specific fragments for Pneumocandin $C_0$ is approximately m/z 507 at collision energies approximately 45-60 V.

9. The method of claim 8, wherein the collision energy is approximately 45-60 V.

10. The method of claim 1, wherein the specific fragments for Pneumocandin $C_0$ is approximately m/z 139, 280 or 338.

11. The method of claim 10, wherein the collision energy is approximately 60 V.

12. The method of claim 1, wherein the specific fragments for Pneumocandin $B_0$ is approximately m/z 300, 416 or 452.

13. The method of claim 1, wherein the specific fragments for Pneumocandin $C_0$ is approximately m/z 338 or 360.

* * * * *